(12) United States Patent
Abramovitch

(10) Patent No.: US 11,244,818 B2
(45) Date of Patent: Feb. 8, 2022

(54) METHOD FOR FINDING SPECIES PEAKS IN MASS SPECTROMETRY

(71) Applicant: Agilent Technologies, Inc., Santa Clara, CA (US)

(72) Inventor: Daniel Y. Abramovitch, Palo Alto, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 428 days.

(21) Appl. No.: 16/224,627

(22) Filed: Dec. 18, 2018

(65) Prior Publication Data

US 2019/0259592 A1 Aug. 22, 2019

Related U.S. Application Data

(60) Provisional application No. 62/632,304, filed on Feb. 19, 2018.

(51) Int. Cl.
*H01J 49/00* (2006.01)
*G06K 9/00* (2006.01)
(Continued)

(52) U.S. Cl.
CPC ........ *H01J 49/0036* (2013.01); *G06K 9/0053* (2013.01); *G01N 30/8634* (2013.01); *G01N 30/8637* (2013.01); *G16C 20/20* (2019.02)

(58) Field of Classification Search
CPC ... H01J 49/0036; G16C 20/20; G06K 9/0053; G01N 30/8634; G01N 30/8637
See application file for complete search history.

(56) References Cited

U.S. PATENT DOCUMENTS 3,954,413 A 5/1976 Kucherov
4,314,343 A 2/1982 Tomlinson
(Continued)

FOREIGN PATENT DOCUMENTS

GB 2390936 A 1/2004
WO 0022649 4/2000
(Continued)

OTHER PUBLICATIONS

Hodgson, et al., Properties, Implementations and Applications of Rank Filters, Feb. 1985, pp. 3-14, vol. 3, No. 1, Image and Vision Computing, Butterworth & Co. Ltd.
(Continued)

*Primary Examiner* — Walter L Lindsay, Jr.
*Assistant Examiner* — Geoffrey T Evans

(57) ABSTRACT

A method for operating a data processing system to find peaks in a mass spectrum that includes an ordered set of measurements of the abundances of species as a function of the mass/charge ratio of the species is disclosed. The method includes selecting a candidate blob that has a plurality of blob peaks from the mass spectrum. The data processing system selects a candidate blob peak for characterization. The candidate blob peak is approximated by a first species peak using a species peak model having a plurality of parameters by fitting the species peak model to a portion of the blob that has values that are substantially free of contributions from other species peaks that overlap with the first species peak and that are not represented by the species peak model. The first species peak is then subtracted from the candidate blob.

20 Claims, 11 Drawing Sheets

(51) Int. Cl.
*G01N 30/86* (2006.01)
*G16C 20/20* (2019.01)

(56) References Cited

U.S. PATENT DOCUMENTS

| | | | |
|---|---|---|---|
| 5,745,369 | A | 4/1998 | Ukon |
| 5,905,192 | A | 5/1999 | Wikfors |
| 6,188,064 | B1* | 2/2001 | Koster .............. H01J 49/0036 |
| | | | 250/281 |
| 6,694,265 | B2 | 2/2004 | Gorenstein |
| 6,870,156 | B2 | 3/2005 | Rather |
| 7,457,708 | B2* | 11/2008 | Thompson ............ G01N 30/72 |
| | | | 702/19 |
| 7,645,984 | B2 | 1/2010 | Gorenstein |
| 7,688,878 | B2 | 3/2010 | Wang |
| 7,983,852 | B2 | 7/2011 | Wright |
| 8,000,959 | B2 | 8/2011 | Kim |
| 8,158,003 | B2 | 4/2012 | Du |
| 8,321,153 | B2 | 11/2012 | Park |
| 8,346,487 | B2 | 1/2013 | Wright |
| 8,372,288 | B2 | 2/2013 | Du |
| 8,428,889 | B2 | 4/2013 | Wright |
| 8,486,268 | B2 | 7/2013 | Du |
| 8,853,623 | B2 | 10/2014 | Verenchikov |
| 8,935,101 | B2 | 1/2015 | Wright |
| 9,406,493 | B2 | 8/2016 | Verenchikov |
| 9,613,786 | B2 | 4/2017 | Yao |
| 9,640,374 | B2 | 5/2017 | Oliphant |
| 2004/0083063 | A1 | 4/2004 | McClure |
| 2004/0199336 | A1* | 10/2004 | Ito ..................... G01N 30/8624 |
| | | | 702/32 |
| 2005/0143948 | A1* | 6/2005 | Ito ..................... G01N 30/8624 |
| | | | 702/134 |
| 2005/0267689 | A1 | 12/2005 | Tsypin |
| 2007/0278395 | A1 | 12/2007 | Gorenstein |
| 2008/0015785 | A1 | 1/2008 | Mujezinovic |
| 2008/0149821 | A1 | 6/2008 | Senko |
| 2009/0177466 | A1 | 7/2009 | Rui |
| 2010/0100336 | A1* | 4/2010 | Wright ................. G16C 20/20 |
| | | | 702/32 |
| 2010/0283785 | A1* | 11/2010 | Satulovsky ........ G01N 30/8624 |
| | | | 345/440 |
| 2011/0282588 | A1 | 11/2011 | Tsypin |
| 2012/0089342 | A1 | 4/2012 | Wright |
| 2012/0166101 | A1 | 6/2012 | Lytle |
| 2012/0246211 | A1 | 9/2012 | Lytle |
| 2014/0088923 | A1 | 3/2014 | Wang |
| 2014/0129496 | A1 | 5/2014 | Campos |
| 2014/0329274 | A1* | 11/2014 | Bowen .................. G01N 33/58 |
| | | | 435/34 |
| 2015/0046096 | A1 | 2/2015 | Wang |
| 2015/0051843 | A1 | 2/2015 | Wang |
| 2015/0074093 | A1* | 3/2015 | Murthy ............ G06F 16/24578 |
| | | | 707/723 |
| 2016/0343561 | A1 | 11/2016 | Verenchikov |
| 2018/0149629 | A1* | 5/2018 | Dasgupta ............ B01D 15/163 |

FOREIGN PATENT DOCUMENTS

| | | |
|---|---|---|
| WO | 2008096962 A1 | 8/2008 |
| WO | 2010141272 A1 | 12/2010 |
| WO | 2011135477 A1 | 11/2011 |
| WO | 2013109314 A1 | 7/2013 |
| WO | 2013/134771 A1 | 9/2013 |

OTHER PUBLICATIONS

Coombes, et al., Improved Peak Detection and Quantification of Mass Spectrometry Data Acquired from Surface-Enhanced Laser Desorption and Ionization by Denoising Spectra with the Undecimated Discrete Wavelet Transform, Nov. 2005, pp. 4107-4117, Departments of Biostatistics and Applied Mathematics, Molecular and Cellular Oncology and Surgical Oncology, The University of Texas M.D. Anderson Cancer Center.

Du, et al., Improved Peak Detection in Mass Spectrum by Incorporating Continuous Wavelet Transform-based Pattern Matching, Jul. 4, 2006, pp. 2059-2065, vol. 22, No. 17 2006, Bioinformatics.

Li, et al., SELDI-TOF Mass Spectrometry Protein Data, 2005, pp. 91-109, Bioinformatics and Computational Biology Solutions Using R and Bioconductor. Statistics for Biology and Health. Springer, New York, NY.

Antoniadis, et al., Peaks Detection and Alignment for Mass Spectrometry Data, Jan. 2010, pp. 17-37, vol. 151 No. 1, Journal de la Societe Francaise de Statistique, France.

Yang, et al., Comparison of Public Peak Detection Algorithms for MALDI Mass Spectrometry Data Analysis, Jan. 6, 2009, volumn 10, issue 1, BMC Bioinformatics 2009.

Yasui, et al., A Data-analytic Strategy for Protein Biomarker Discovery: Profiling of High-dimensional Proteomic Data for Cancer Detection, 2003, pp. 449-463, Biostatistics, Great Britain.

Kuehl, Accurate Mass and Spectral Accuracy of Agilent LC/MS Single Quadrupole Systems with Cerno MassWorks, Application Notes, 2017, Agilent Technologies, Inc., Santa Clara, CA.

Prest, et al., Cerno Bioscience MasWorks: Acquiring Clibration Data on Agilent GC/MSDs, Application Note, 2009, Agilent Technologies, Inc., Santa Clara, CA.

Wang, et al., GC/MSD Formula Determination for Forensic Chemistry, Cerno Application Note, Oct. 2009, Cerno Bioscience, Danbury, CT.

Gu, et al., Accurate Mass Measurements on Unit Mass Resolution Mass Spectrometers, 2005, Cerno Bioscience, New Haven, CT.

Wang, et al., Comprehensive Mass Spectral Calibration to Achieve High Mass Accuracy and Parameter Free Peak Detection, 2005, Cerno Bioscience, New Haven, CT.

Kuehl, et al., Comparing Mass Defect Filtering and Accurate Mass Profile Extracted Ion Chromatogram (AMPXIC) for Metabolism Studies, 2006, Cerno Bioscience, Danbury, CT.

Wang, et al., Processing Raw Mass Spectral Data for High Mass Accuracy, 2006, Cerno Bioscience, Danbury, CT.

Gu, et al., Automated and Parameter-Free Peak Integration for LC/MS/MS Quantitation, 2006, Cerno Bioscience, Monmouth Junction, NJ.

Ma, et al., Automatic Generation of Extract Ion Chromatogram for Mass Spectral Peaks with Specific Isotope Labeled Patterns, 2007, Cerno Bioscience, Plainsboro, NJ.

Zhang, et al., Metabolite Identification Using a Unit Mass Resolution Liquid Chromatography/Mass Spectrometry with Accurate Formula Identification and Mass Defect Filtering, 2008, Wyeth Research, Princeton, NJ.

Gu, et al., High Mass Accuracy Measurements and Elemental Composition Determination of Molecular Ions of Pesticides with a Single Quadrupole GC/MS System, 2015, Cerno Bioscience, Norwalk, CT.

Gu, et al., Quantitative Analysis of Post Translation Modification of Protein Therapeutics at a Subunit Level by Spectral Deconvolution, 2015, Cerno Bioscience, Norwalk, CT.

Gu, et al., The Creation and Unknown Search of Accurate Mass Library with GC/MS Quadrupole Systems, 2016, Cerno Bioscience, Norwalk, CT.

Zhao, et al., Direct and Accurate Quantitation of Labeled and Un-Labeled Ions with LC/MS, 2016, slides 1-17, XenoBiotic Laboratories, Inc., Plainsboro, NJ.

Andrews, et al., A Software Tool to Automatically Evaluate Scan-by-Scan Spectral Accuracy of Ultra High Resolution LC/MS Data for Unique Elemental Composition Determination, 2016, Cerno Bioscience, Norwalk, CT.

Wang, Peak Shape Calibration and Formula Determination on an AccuTOF DART System, Application Note No. 104, Apr. 2008, Cerno Bioscience, Danbury, CT.

Zhou, et al., Direct and Accurate LC/MS Quantitation of Ring Labeled Compounds, 2017, WuXi AppTec, Plainsboro, NJ.

Wang, et al., Towards More Robust, Accurate, and Automated GC/MS Counpound ID, 2017, Cerno Bioscience, Norwalk, CT.

(56) References Cited

OTHER PUBLICATIONS

Fung, et al., ProteinChip Clinical Proteomics: Computational Challenges and Solutions, Product & Technology Report, Mar. 2002, Ciphergen Biosystems, Fremont, CA.

* cited by examiner

METHOD FOR FINDING SPECIES PEAKS IN MASS SPECTROMETRY

RELATED APPLICATIONS

This application claims priority from U.S. Provisional Application 62/632,304 filed Feb. 19, 2018.

BACKGROUND

Mass spectrometers separate ions generated by an ion source based on the mass-to-charge ratio of the ions. The output of a mass spectrometer is typically a plot of the abundance of each ion as a function of the mass/charge ratio of that ion, denoted by m/z. An ion species that is present in sufficient quantity relative to the noise in the spectrum typically generates a peak in the spectrum. This peak is characterized by a width along the m/z axis and a height. The area under that peak represents the number of the ions with the corresponding m/z. A spectrum can include a large number of such peaks. The height of the peak is sometimes referred to as the abundance of the ions.

Unfortunately, the width of the peaks can be greater than the separation of the peaks along the m/z axis, and hence, a local maximum in the spectrum that is above a noise floor could be the result of more than one ion species. Determining the abundance of each ion species that makes up such an overlapping peak structure in a spectrum presents significant challenges. Ideally, this process would be done in real time using the data processing system that also runs the mass spectrometer and interacts with the user. This allows the operator to track changes in the spectrum peaks during the tuning of the system. However, the computational capabilities of such real time controllers are limited.

SUMMARY

The present invention is directed to a method for operating a data processing system to find peaks in a mass spectrum which includes an ordered set of measurements of the abundances of species as a function of the mass/charge ratio of the species and computer readable media that cause a data processing system to execute that method. The method includes selecting a candidate blob that has a plurality of blob peaks from the mass spectrum, and selecting a candidate blob peak from the plurality of blob peaks for characterization.

A first species peak is approximated by a species peak model having a plurality of parameters by fitting the species peak model to a portion of the candidate blob that has values that are substantially free of contributions from other species peaks that overlap with said first species peak and that are not represented by said species peak model. Said first species peak is then subtracted from the candidate blob.

In one aspect of the invention, the blob peaks are characterized by a dominant blob peak and wherein the dominant blob peak is selected as the candidate blob peak.

In another aspect of the invention, the blob peaks are characterized by first and second edge blob peaks, and the candidate blob peak is one of the first and second edge blob peaks.

In another aspect of the invention, the steps of selecting a candidate blob peak for characterization include approximating the first species peak by a species peak model and subtracting the first species peak from the candidate blob. These steps are repeated until there are no more peaks in the candidate blob that can be approximated by a species peak model.

In another aspect of the invention, the candidate blob is displayed with the species peaks associated with the candidate blob superimposed on the candidate blob.

In another aspect of the invention, the species peak model is characterized by a plurality of model parameters, the candidate blob peak is characterized by a blob peak amplitude and a center m/z value, and approximating the first species peak comprises determining the model parameters from the blob peak amplitude, the center m/z value, and one other point on the blob.

In another aspect of the invention, the species peak model includes a function chosen from the group consisting of Gaussian, two-slope Gaussian, Gamma, Poisson and Rayleigh functions.

In another aspect of the invention, approximating the first species peak by a species peak model comprises fitting a portion of the candidate blob to a two-species peak model characterized by first and second species peaks with the first species peak corresponding to the candidate blob peak.

In another aspect of the invention, approximating the candidate blob peak by a species peak model comprises fitting a portion of the candidate blob to a three-species peak model characterized by said first species peak, a second species peak, and a third species peak with the first species peak corresponding to the candidate blob peak.

In another aspect of the invention, the candidate blob is filtered through a low-pass filter prior to selecting the candidate blob peak for characterization.

In another aspect of the invention, the data processing system is part of a built-in controller that controls a mass spectrometer.

DETAILED DESCRIPTION

Figure 8:
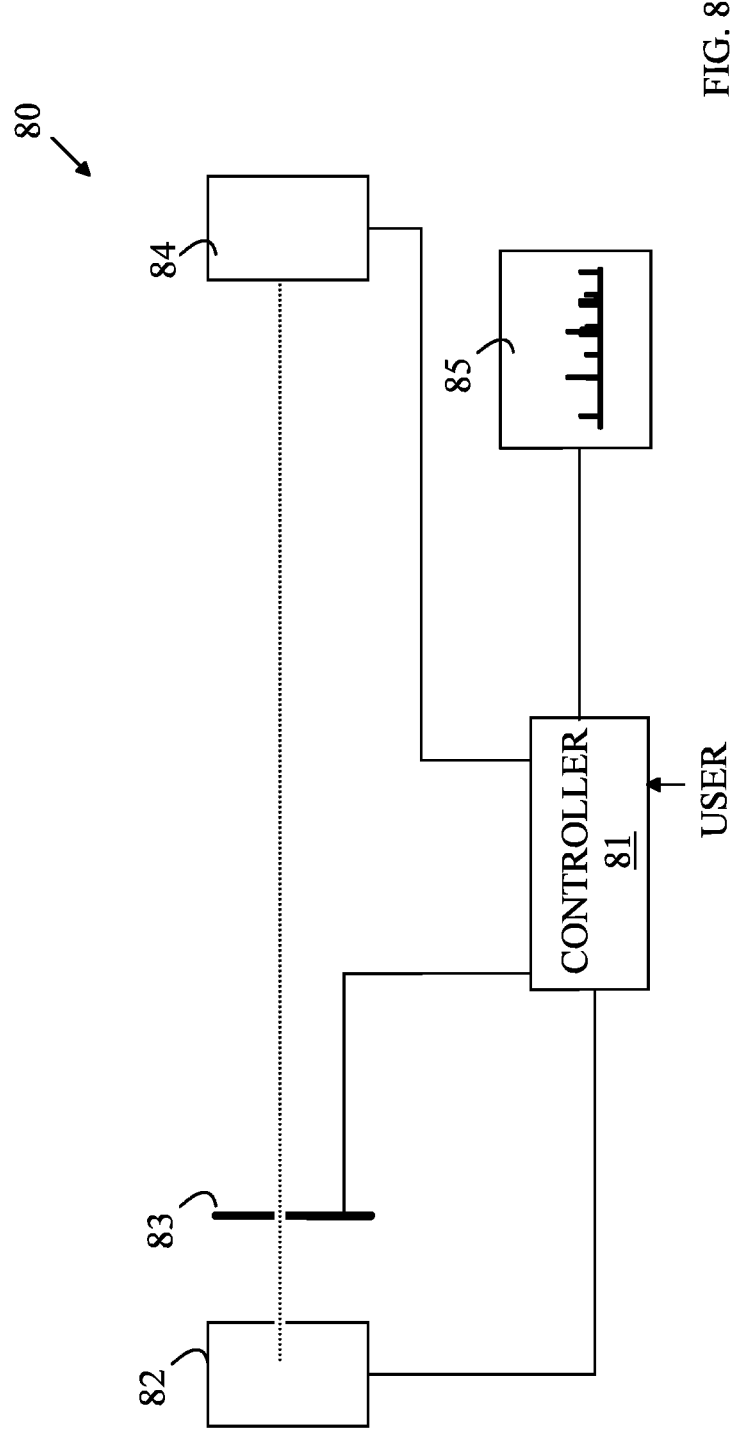
FIG. 8 illustrates a typical time-of-flight mass spectrometer that utilizes an embodiment of the present invention to detect ion abundances.

The manner in which the present invention provides its advantages can be more easily understood with reference to FIG. 8, which illustrates a typical time-of-flight mass spectrometer 80 that utilizes an embodiment of the present invention to detect ion abundances. Mass spectrometer 80 includes an ion source 82 that generates ions from a sample that is to be analyzed. The ions are accelerated by providing a short high voltage pulse between ion source 82 and an electrode 83. The ions leaving electrode 83 travel over a path and are detected by a detector 84 at the end of that path. The time to traverse the path depends on the mass-to-charge ratio (m/z) of the ions, ions with smaller m/z values arriving at detector 84 first. A controller 81 controls the application of the voltage pulse and measures the time of flight of the particles by detecting the time difference between the voltage pulse and the arrival of the ions at detector 84. The mass spectrometer 80 typically includes a user interface that includes a display 85 on which a spectrum comprising a plot of the number of ions detected as a function of m/z of the ions is displayed. The user uses the display 85 to tune the instrument and the ion source 82. Controller 81 typically includes a general purpose data processing system.

To simplify the following discussion, a time-of-flight mass spectrometer will be utilized. However, the present invention can be applied to other types of mass spectrometers. For the purposes of this discussion, a mass spectrometer is defined to be an apparatus that separates charged ions based on the m/z value of the ions, detects the ions after separation, and generates a spectrum comprising the number of the detected ions as a function of m/z. The number of detected ions for a given m/z value is often referred to as the "abundance" of the ions. In the case of a time-of-flight mass spectrometer, the ions are separated by their time of flight from the source to the detector.

Figure 9:
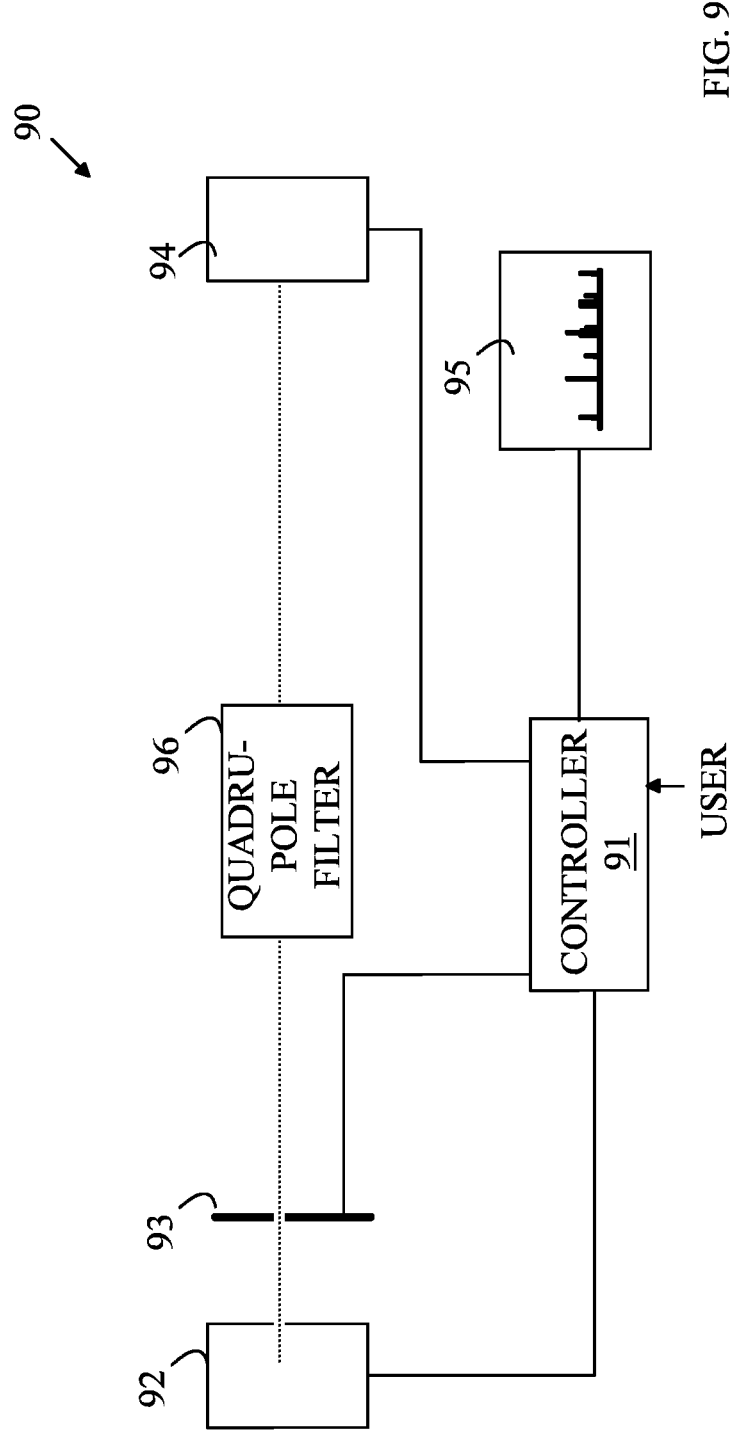
FIG. 9 illustrates a typical quadrupole mass spectrometer that utilizes an embodiment of the present invention.

Refer now to FIG. 9, which illustrates a typical quadrupole mass spectrometer 90 that utilizes an embodiment of the present invention. Mass spectrometer 90 includes an ion source 92 that generates ions from a sample that is to be analyzed. The ions are accelerated by providing a high voltage between ion source 92 and an electrode 93. The ions leaving electrode 93 travel over a path that includes a quadrupole filter 96 that selects ions having an m/z value in a particular band. The ions leaving quadrupole filter 96 are detected by a detector 94. A controller 91 controls the accelerating voltage and measures the ions leaving the quadrupole filter 96. Controller 91 steps the center of the bandpass of the quadrupole filter 96 and the width of the pass window to generate a spectrum that is displayed on a display 95. The mass spectrometer 90 typically includes a user interface that includes the display 95 on which a spectrum comprising a plot of the number of ions detected as a function of the m/z of the ions is displayed. The user uses the display 95 to tune the instrument and the ion source 92. Controller 91 typically includes a general purpose data processing system.

Figure 1:
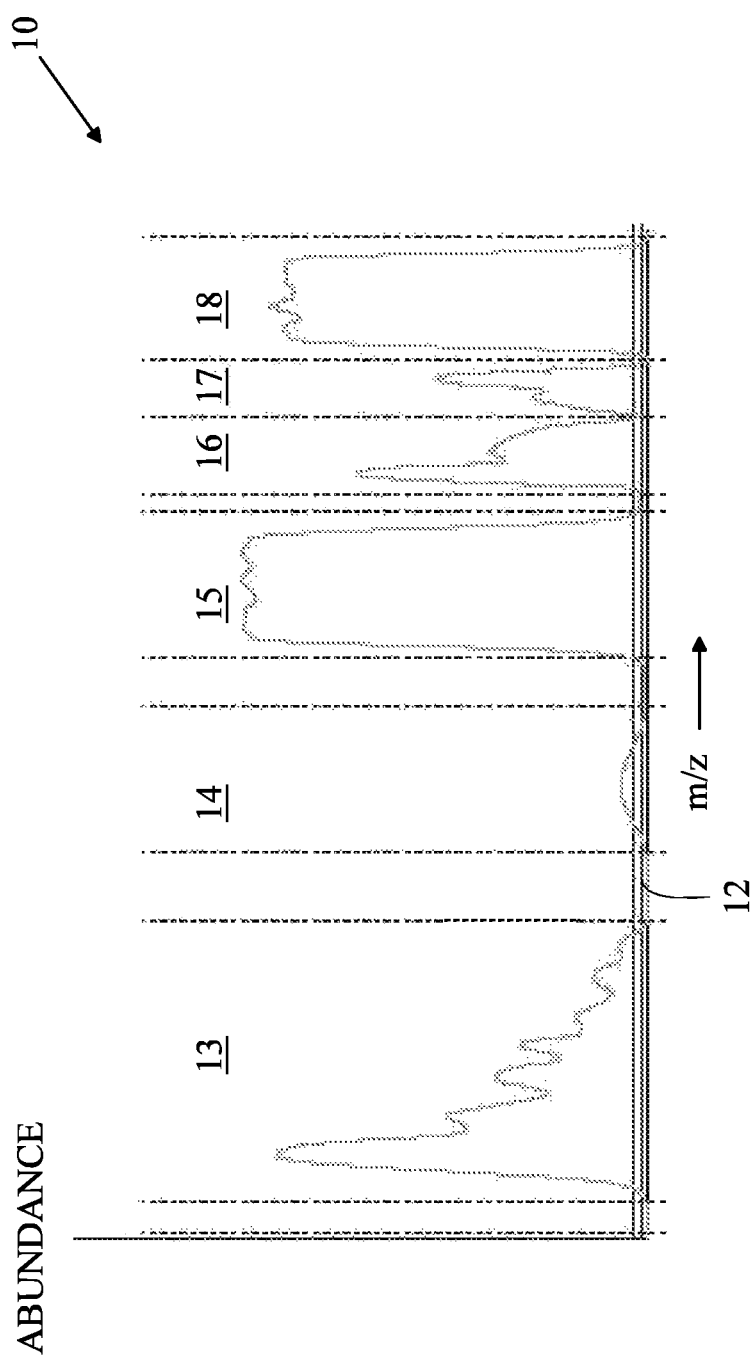
FIG. 1 illustrates the types of structures found in exemplary mass spectrometer spectrums.

Refer now to FIG. 1, which illustrates the types of structures found in exemplary mass spectrometer spectrums. To simplify the following discussion, a "blob" is defined to be a region of the spectrum in which all m/z samples are above a blob threshold. A blob can be the result of a single underlying peak representing a single ion species or a group of overlapping peaks, each peak being the result of an underlying single ion species in which the differences in m/z values are less than the widths of the peaks. Referring to FIG. 1, spectrum 10 includes blobs shown at 13-18. The noise threshold or baseline representing an abundance of zero is shown at 12. Blobs can have different shapes depending on the sample and the manner in which the mass spectrometer is tuned. The blobs at 13, 16, and 17 would appear to include multiple peaks. While the blob at 14 appears to be a single peak, the flat topped peaks at 15 and 18 could involve a number of closely spaced peaks or be an artifact of the tuning of the mass spectrometer.

It should be noted that not all types of blobs are present in all spectrums. For example, when a quadrupole mass spectrometer is tuned by changing the bandpass of the m/z filter or when the instrument is being calibrated and tuned, the types of blobs and the shapes of the blobs will, in general, change.

In general, all of the ions having m/z values in a small window or "bin" of m/z values are outputted. In this case, the spectrum consists of a number of discrete values representing the number in each bin. Ideally, the spectrum from a sample having a single ion species would consist of a peak that fits within a single bin or into two adjacent bins in the case in which the m/z value is on the boundary of two bins. However, in practice, the spectrum generated by such a single species is much broader. The additional breadth is generated by the finite resolution of the mass spectrometer. For example, in a time-of-flight spectrometer, the electric field that accelerates the ions can vary with the position of the ion in the ion source, and the distance over which the ion travels can vary slightly depending on the position of the ion in the ion source when the accelerating pulse is applied to the ions. Hence, a spectrum for a single ion species will appear significantly broader than the ideal case discussed above.

If the sample being analyzed consisted of a single species of ions, the spectrum would consist of a single peak at the m/z value that characterizes that species. The shape of the peak can be modeled by various functions. To simplify the following discussion, a Gaussian function will be assumed of the form:

$$a(x, A, M, \sigma) = A e^{-(M-x)^2 / 2\sigma^2} \quad (1)$$

To simplify the notation, x=m/z. Here, A measures the maximum abundance of the species, M is the mean m/z value that characterizes the peak and σ is the standard deviation of the Gaussian. As the spectrometer is tuned, σ will vary. Given a blob peak that is the result of a single species of ions, the parameters A, M, and σ can be determined by fitting the measured abundances as a function of x to the Gaussian function of Eq. (1) using a conventional fitting algorithm.

The goal of the present invention is to decompose the spectrum, as far as possible, into a plurality of underlying species peaks of the form shown in Eq. (1) while keeping the computational workload of the decomposition within the capabilities of the data processing system that are part of the mass spectrum analyzer's controller.

In general, a blob has a number of peaks that are visible as each of these peaks is located at an apex of the blob. These peaks will be referred to a blob peaks in the following discussion. Each blob peak is the result of a peak in the species abundance spectrum. The species abundance spectrum is defined to be the spectrum that would be generated by a single ion species having a single m/z value. The peak produced by this single ion species will be referred to as a species peak in the following discussion. If a blob has one peak resulting from an underlying species peak, then the blob and the species abundance spectrum will be the same. Except in the case of a blob that has single ion species peak, a blob will be the result of a plurality of single ion species peaks that overlap one another. Some of the blob peaks will be the result of an underlying species peak; however, there also may be underlying species peaks that do not generate a blob peak.

A blob is a sequence of observed abundance values. A given abundance value could be from a point on a single species peak of an underlying species peak or from the sum of values on two or more overlapping species peaks. Most of the values that make up a blob are the result of overlapping species peaks, and hence, the species peaks cannot be determined from these values without fitting the blob to the model having at least one species peak centered at each blob peak, and even this model will be insufficient if there is a small species peak that is "buried" in the blob in a manner that does not generate a peak in the blob. This approach also requires significantly more computing resources.

In one aspect of the present invention, this decomposition is performed by identifying a potential single species peak in a blob corresponding to one of the blob peaks, verifying that the parameters of the candidate species peak can be determined from the blob values in a region of the blob peak, calculating the parameters of a model for the species peak, and subtracting that model peak from the spectrum. The procedure is iterated until all peaks that can be so modeled are removed and the blob is emptied of peaks. The analysis of the blobs is done one blob at a time, since peaks in other blobs do not significantly overlap the peaks in the blob currently being analyzed.

The present invention assumes that a blob peak in a multi-peak blob is the result of an underlying species peak that has been "contaminated" by one or more other species peaks in the blob. If the contamination is small, the blob values in the region of the blob peak can be used to compute the parameters on a single species peak model that will adequately represent the underlying species peak corresponding to that blob peak. The computed model peak can then be subtracted from the blob leaving a simplified blob. The simplified blob can then be subjected to the same analysis. Ideally, the process can be repeated until no identifiable blob peak is left in the residual blob. The various species peaks can then be provided to the user of the mass spectrometer. For example, the model species peaks can be overlaid on the spectrum generated by the mass spectrometer.

Figure 2:
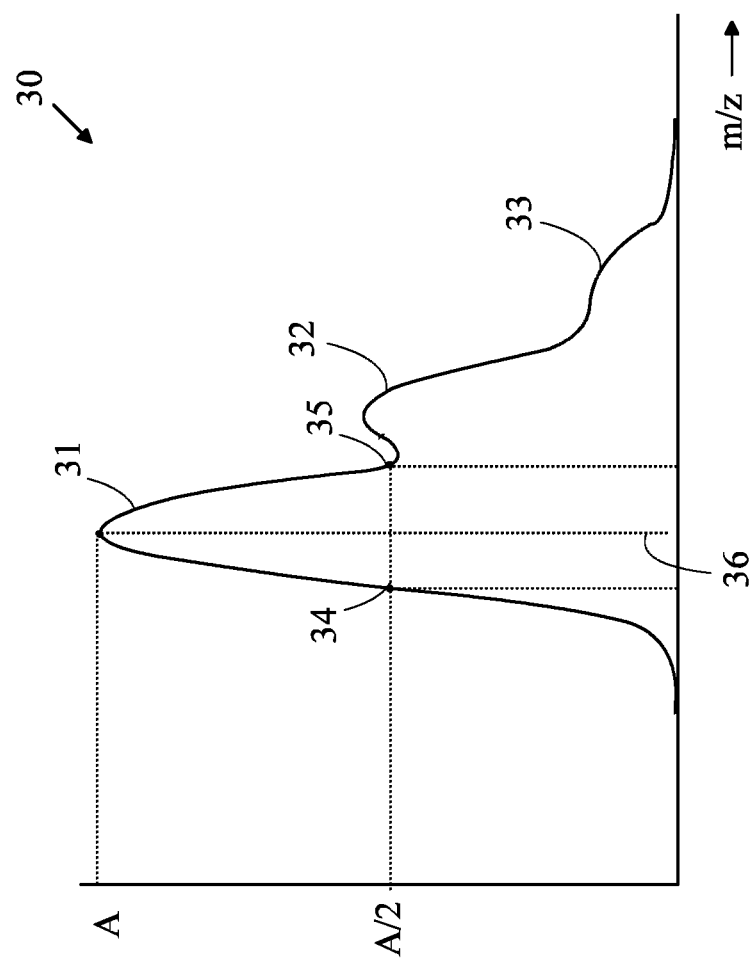
FIG. 2 illustrates a two-peak blob resulting from underlying species peaks corresponding to blob peaks 31-32.

This decomposition process depends on finding a portion of the blob that only contains data from a single species peak. A portion of the blob is defined to be substantially free of contamination from other species peaks if the determined single peak model parameters are substantially equal over different parts of that portion. Refer now to FIG. 2, which illustrates a two-peak blob resulting from underlying species peaks corresponding to blob peaks 31-32. Blob 30 also has a hidden peak 33 for which a blob peak is not present. As will be explained in more detail below, the species peak corresponding to blob peak 31 is contaminated by the low m/z tail of the species peak corresponding to blob peak 32. While the region between blob peak 31 and blob peak 32 is unlikely to be usable for calculating the parameters of a single peak model due to this contamination, a portion of blob peak 31 along the leading edge of blob peak 31 may be substantially free of contamination. In one embodiment of the invention, the single peak model has only three parameters. Hence, absent noise, any three points on the leading edge of blob peak 31 could be fitted to the model and model parameters determined. In the presence of noise, the number of blob points needed is somewhat larger. Consider a sliding window that moves along the leading edge of blob peak 31 with sufficient points in the window to determine the model parameters of the model corresponding to Eq. (1). If the values of the model parameters do not change significantly as the window proceeds along the leading edge, the regions traversed are free of contamination and can be used to calculate the model parameters. The parameters will be defined as being substantially the same if the variations in the parameters from window position to window position vary by no more than expected from noise in the blob values.

If a blob remains for which the underlying species peak cannot be reliably computed using a single peak model, a more complex model is utilized in which the species peak to be computed is one of a plurality of species peaks that are fitted to a portion of the blob. In this case, one of the model species peaks represents the species peak of interest, and the other(s) correct for distortions of neighboring peaks. The species peak of interest can then be reliably subtracted from the blob leaving a simplified blob that becomes a candidate for decomposition by one species peak model.

Figure 11:
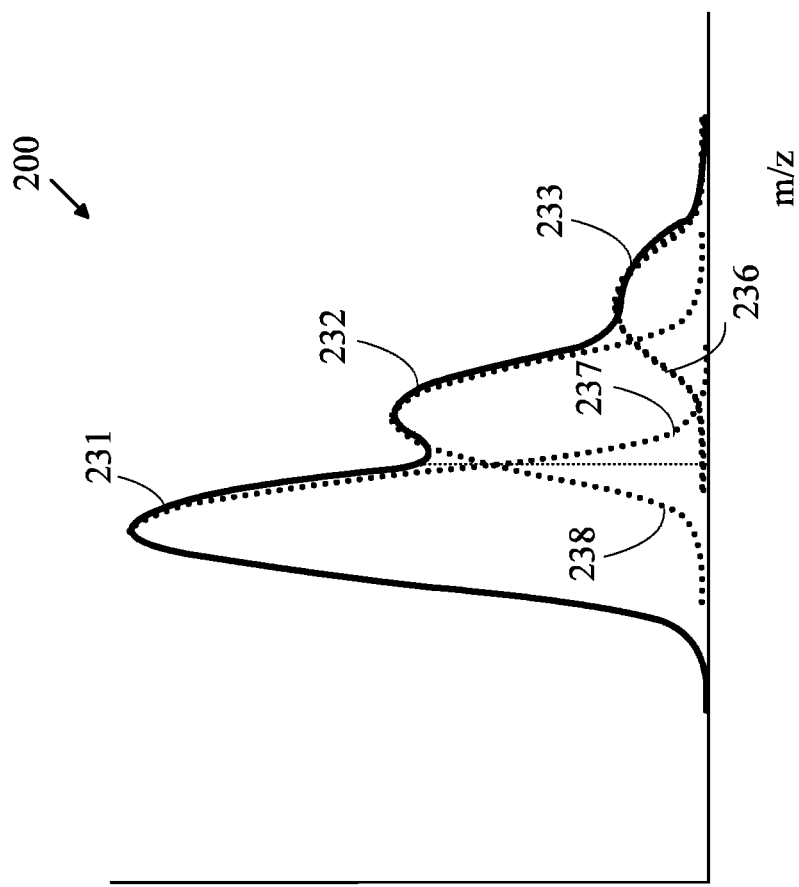
FIG. 11 illustrates a two-blob peak blob and the underlying species peaks shown at 236-238.

Refer now to FIG. 11, which illustrates a two peak blob and the underlying species peaks shown at 236-238. For the purposes of this discussion, a blob peak is defined to be a region of the blob that when traversed from left to right increases, reaching a maximum value and decreasing after the maximum value. Algorithms for finding the blob peaks in the presence of noise will be discussed in more detail below. Using this definition, peaks 231 and 232 are blob peaks. The region shown at 233 is not a blob peak, even though there is an underlying species peak 236.

A blob is not a collection of isolated species peaks because the species peaks are close enough to each other to interfere with each other in the sense that the blob data in the part of the blob corresponding to the species peak is the sum of a plurality of species peaks. The goal of a single species peak decomposition algorithm utilizing a single species peak model is to find a region of the blob which is substantially the result of only one species peak. That is, the underlying contamination of the species peak by neighboring peaks is sufficiently small to allow the parameters of the species peak of interest to be computed from the blob abundance data in the region of the blob peak corresponding to the species peak of interest without modeling the entire blob as a series of species peaks. In blob 200, the region between blob peaks 231 and 232 is the result of the sum of species peaks 237 and 238 as evidenced by the fact that the blob does not return to the base line before reaching blob peak 232; hence, this region is not a suitable region to compute the parameters of species peak 237 using a single peak model.

The region on the leading edge of blob peak 231, however, is not contaminated by species peak 238, and hence, can be used to compute a single peak model of species peak 237. The manner in which the portion of the data in the vicinity of a blob peak is identified to determine regions which are substantially free of competing species peaks, and hence, useable in a single peak model, will be discussed in more detail below.

Figure 10:
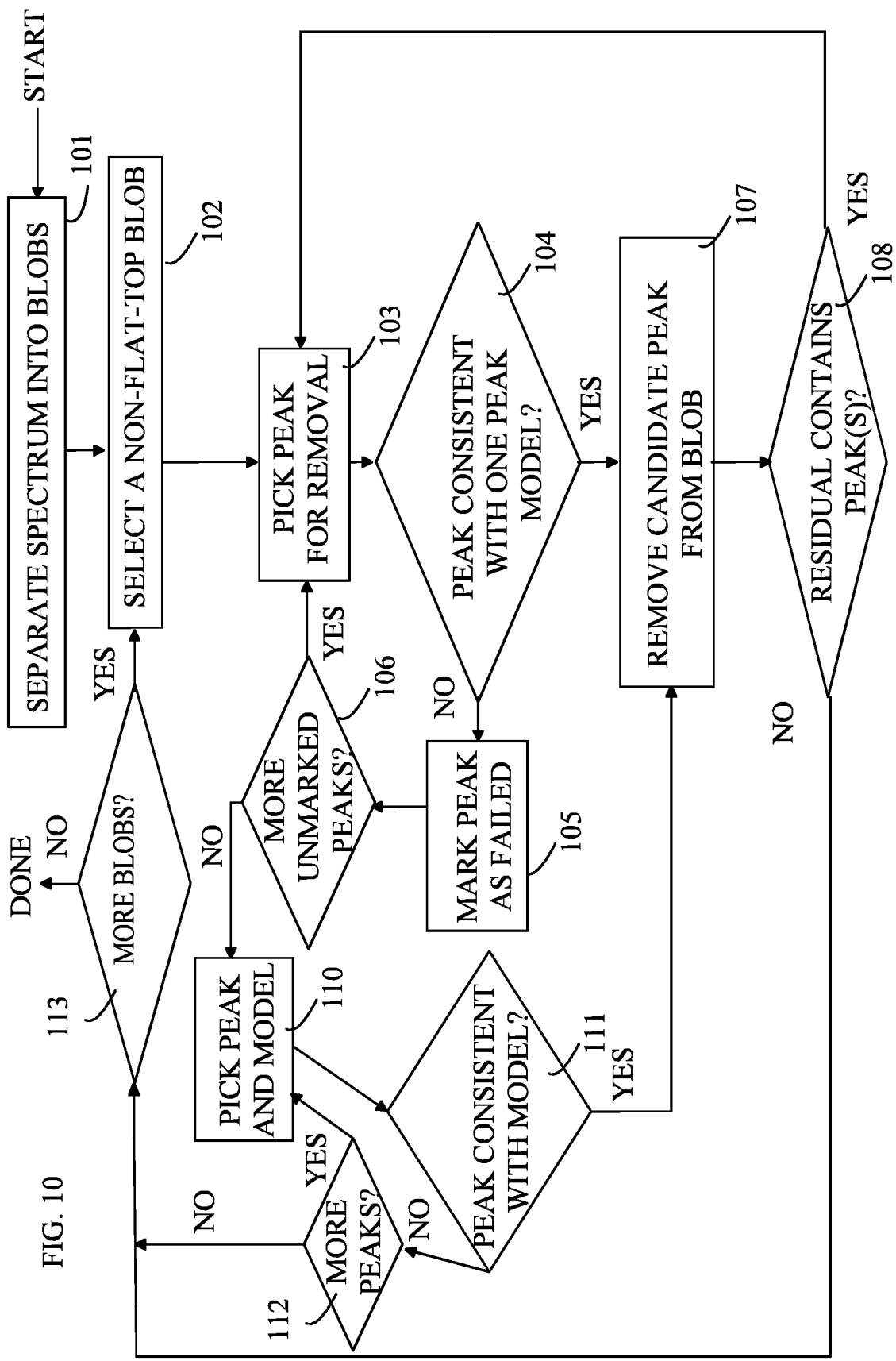
FIG. 10 is a high level flow chart of one embodiment of the method of the present invention.

Refer now to FIG. 10, which is a high level flow chart of one embodiment of the method of the present invention. Initially, the present invention separates the mass spectrum into blobs as shown at 101. In general, the blob threshold is greater than the baseline for the spectrometer. For the purposes of the present discussion, the baseline is the level corresponding to an abundance of zero above the noise level. Since the mass spectrometer has a finite level of noise, the blob threshold must be set above the baseline plus the expected noise to prevent a number of "noise" blobs from being identified and/or negative valued signals being generated.

In one aspect of the invention, blobs are initially detected by searching for regions above the blob threshold. Once those blobs are found, the edges of the blobs are refined by searching down to where the abundance gets suitably close to the baseline. This allows the tails of the blob to be determined without also generating "noise" blobs. If a blob extends to one of the edges of the spectrum, the blob is defined to begin or end on the edge in question.

In some cases, there can be ambiguity as to the end point of a blob when two blobs are separated by a small range of m/z values. Consider the blob at the lower m/z value that is to be extended at the high m/z value of the blob. As that blob is extended upward in m/z values, the edge can cross the extension of the lower tail of the higher m/z blob. In this case, the high edge of the first blob can be defined to be at the halfway point between the originally identified blobs. Similarly, the lower edge of the second blob is defined to be at this halfway point.

Once the blobs have been identified, the present invention proceeds to classify each blob. The classification starts by determining the maximum abundance in each blob. The range between the baseline and the maximum value for a blob is then divided into three equal ranges. The first range extends from the baseline to one-third of the maximum value; the second range extends from the maximum of the first range to two-thirds of the maximum value, and the third range extends from the maximum of the second range to the maximum value.

There are three types of blobs. A single peak blob, a multi-peak blob and a flat-top blob. A flat-top blob is defined to be a blob that has a high percentage of its abundance values in the third range. In one aspect of the invention, a blob with 80 percent or more of its abundance values in the third range is defined to be a flat-top blob. In another aspect of the invention, a blob with 90 percent of its abundance values in the third range is defined to be a flat-top blob. In yet another aspect of the invention, a blob with 70 percent of its abundance values in the third range is defined to be a flat-top blob.

In general, flat-top blobs are not easily decomposed into underlying single species peak functions, and hence, the present invention merely saves the parameters that characterize the flat-top blob, such as its position, height, etc.

To avoid confusion in the following discussion, two types of peaks need to be distinguished, peaks or apexes in the abundance values of a blob, which are referred to as blob peaks, and single peaks determined by fitting the species model to a portion of the blob, which will be referred to as species peaks.

Referring again to FIG. 10, after decomposing the spectrum into blobs, the present invention selects a non-flat-top blob for processing as shown at 102. Once the blob is identified, this embodiment of the present invention selects a candidate peak within the blob and attempts to fit that candidate peak to a species peak using a single species peak model as shown at 103. The present invention first finds the blob peaks in the selected blob. The manner in which the blob peaks are found will be discussed in more detail below. For the purposes of the present discussion, one of the blob peaks is chosen and an attempt to fit that peak to a model having one species peak is made. If the blob peak is consistent with a single species peak as shown at 104, the parameters of the one-species peak model are determined and that peak is removed from the blob by subtracting the species peak model from the blob as shown at 107. The data processing system then checks for a residual blob that could contain another species peak as shown at 108. If a peak remains, a new blob peak is selected for evaluation and removal (step 103).

If the blob peak is not consistent with a one-species peak model, the blob peak is marked as having failed as shown at 105. If there are more unmarked blob peaks in the current blob (step 106), one of the unmarked peaks is chosen and the process repeats starting from step 103.

If there are no more unmarked blob peaks in the current blob, one of the failed blob peaks is chosen for fitting using a higher order model as shown at 110. If the blob peak is consistent with the higher order model, the single peak portion of the model is used to remove the peak from the blob as shown at 111 and 107. In this case, the residual blob is once again checked for blob peaks that might be evaluated and removed.

If the blob peak fails the higher order model, another blob peak is selected in that blob and the process is repeated as shown at 112 and 110. If there are no more blob peaks to test in the residual of the current blob, a new blob from the blob list is selected as shown at 113 and 102. If there are no more blobs to be tested, this part of the method exits.

The above-described method requires that a blob be chosen and that peaks within the currently selected blob be chosen. The blob that is chosen for processing can be chosen using many different algorithms. For example, the blobs can be chosen in the order of the m/z value at the beginning of the blob. In another example, the blobs and the species models that have been found to date are displayed to a user and the user selects the next blob to be processed.

Once a blob has been chosen, the order in which the blob peaks are chosen for fitting to a species model must be set. In one aspect of the invention, the dominant blob peak, i.e., the blob peak having the maximum amplitude, is chosen. The dominant blob peak is chosen because the underlying species peak is less likely to be distorted by adjacent peaks in a manner that prevents the parameters of the single species peak to be determined. If the species peak cannot be reliably fit to a one species peak model, the blob peaks on the edge of the blob are tested next, as these peaks are less likely to be distorted from a neighboring peak on one side of the chosen peak, and hence, may present sufficient points to fit the blob peak to a single species peak.

Refer again to FIG. 2. Peak 33 is not a blob peak in that it does not have a local maximum. This type of peak will be referred to as a hidden peak in the following discussion. Blob peak 31 is the dominant blob peak.

Having selected the dominant blob peak 31, the data processing system proceeds to test the peak to determine if it can be used to compute the parameters of the underlying species peak. As noted above, a portion of the blob associated with the underlying species peak must be free from "contamination" from a neighboring species peak so that a portion of the blob data can be used to determine the parameters that define the species peak model.

In the present example, the underlying species peak is assumed to be Gaussian having the form shown in Eq. (1). One aspect of a Gaussian that is easily tested is the symmetry of the function about the center of the species peak. In one aspect of the present invention, the data processing system searches forward and backward from the dominant blob peak at 36 until the location of some predetermined amplitude point is reached. For the purposes of this example, it will be assumed that the half-height points shown at 34 and 35 are the points in question. However, other amplitude points could be utilized.

If the search on one side encounters another blob peak before reaching predetermined amplitude points, there is an adjacent species peak that is close enough to prevent the blob data to be used to fit the single species peak model from being determined from the blob data on that side of the blob peak, and hence, that side of the blob peak cannot be utilized in determining the parameters of the underlying species peak.

If the search reaches the amplitude points which in this example are the half-width points, the half-widths of the peak on each side of the blob peak maximum are determined. The left half-width is the absolute value of the difference between the m/z coordinates of points 34 and 36. The right half-width is the absolute value of the difference between the m/z coordinates of points 36 and 35. In the present example, it is noted that the half-width values are different. In particular, the left half-width is less than the right half-width. This indicates that blob peak 31 is being broadened on the right of the blob peak by the tail of blob peak 32. Hence, the right half of blob peak 31 cannot be reliably utilized to determine the parameters of the underlying species peak as the blob data is at least the sum of the two underlying species peaks on the right side of the maximum.

It still may be possible to determine the parameters of the underlying species peak from the left edge of the candidate peak. In one aspect of the invention, it is assumed that the blob peak height and the blob peak position are the same as the amplitude and center of the underlying species peak, respectively. In this case, a value for $\sigma$ can be obtained from any point on the left edge of blob peak 31 by a simple table lookup. Denote the value of $\sigma$ obtained by measuring the height at the point m/z by $\sigma(m/z)$. In the absence of noise, the function $\sigma(m/z)$ should be constant for various m/z values if the distortions introduced by the adjacent peak are not substantial. If the function has a region in which $\sigma(m/z)$ is substantially constant, the average of $\sigma$ values of that region can be used to obtain the final parameter of the underlying species peak. Using the average value of $\sigma(m/z)$ reduces errors resulting from noise. If no such region can be found, then the peak is inconsistent with a single peak model. If the blob peak in question is inconsistent with the single peak model, the remaining peaks are tested to determine if another candidate peak is available as shown at 106. If no remaining peaks are consistent with the single peak model, a higher order model must be utilized. Such higher order models will be discussed in detail below.

Figure 3:
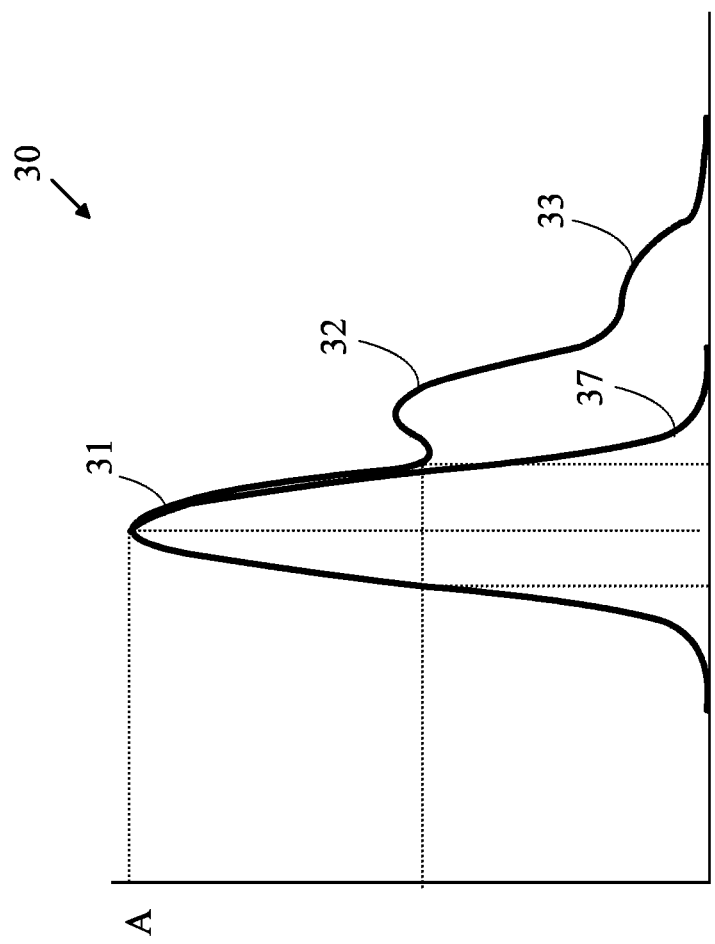
FIG. 3 illustrates the blob of FIG. 2 with the approximation to the species peak 37 obtained from the single species peak model that underlies dominant blob peak 31.
Figure 4A:
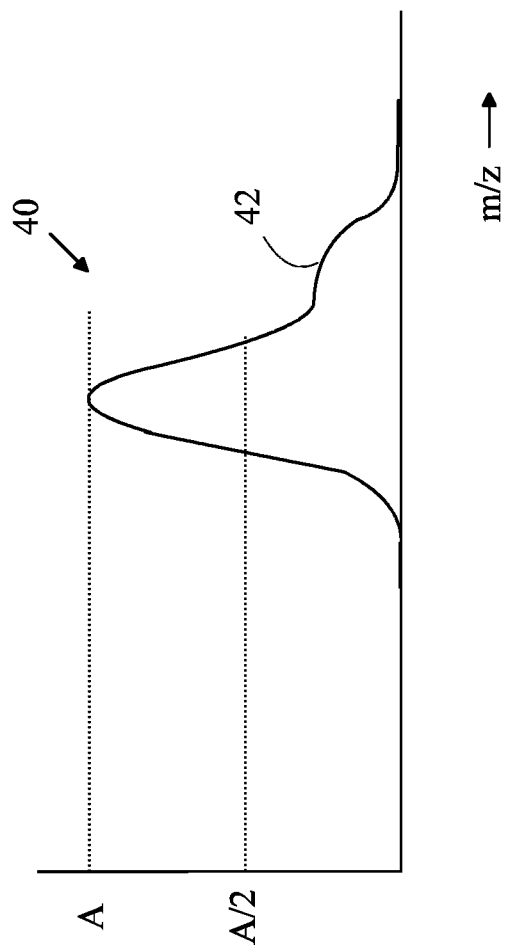
FIG. 4A illustrates the residual blob 40 that is left when the approximation of series peak 37 is subtracted from blob 30.

For the purposes of this example, it will be assumed that blob peak 31 can be used to compute the parameters of the underlying species peak. Refer now to FIG. 3, which illustrates the blob of FIG. 2 with the approximation to the species peak 37 obtained from the single species peak model that underlies dominant blob peak 31. The approximation of species peak 37 is then subtracted from blob 30 leaving the residual blob 40 shown in FIG. 4A. Since the data processing system notes that there is a residual blob, the residual blob is searched again for blob peaks as candidates for modeling and removal.

Figures 4B, 5:
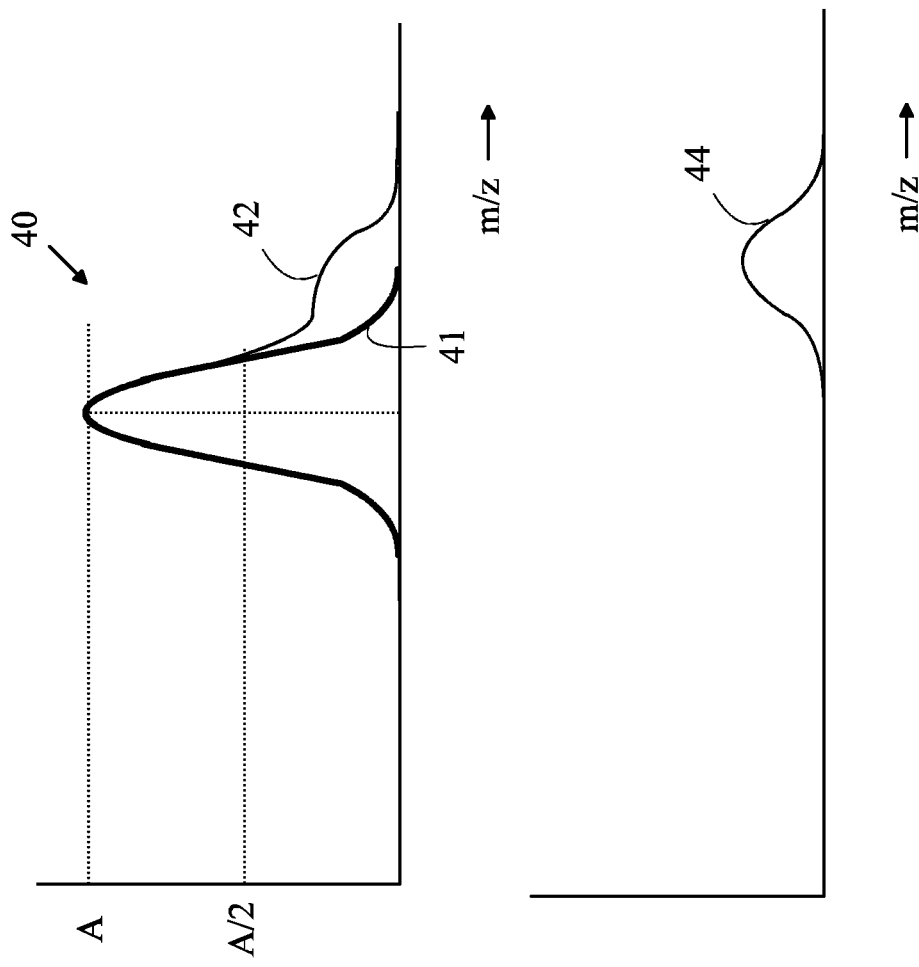
FIG. 4B illustrates the processing of that residual blob.
FIG. 5 illustrates the residual blob when the species peak is subtracted from blob 40.

Refer now to FIG. 4B which illustrates the processing of that residual blob. In this case, the half-width at half maximum is the same for the portion of the curve on each side of the dominant peak, and hence, the estimate of $\sigma$ can be obtained from the full width at half maximum. The estimates for A and M are the amplitude and position of the maximum in the blob. The model can again be tested and refined as described above for the first peak before subtracting the peak from the residual blob. That is, the $\sigma$ obtained from using the full width at half maximum matches that obtained using other points at different abundances. The resultant species peak is shown at 41. The species peak is subtracted from residual blob 40 leaving the residual blob shown at 44 in FIG. 5, which is the remainder of residual blob 40 after the subtraction. This residual blob is then searched for new blob peaks which can be modeled and removed, leaving a new residual blob. In the example of FIG. 5, if the newly revealed peak in the residual blob, 44, meets the selection criteria, it can be modeled and removed from the blob. This process is iterated until there are no discernable peaks left in the blob that are capable of being modeled by a species peak.

It should be noted that the hidden peak at 42 does not become a blob peak until after species peak 41 is removed from the blob. Hence, the number of species peaks needed to represent a blob cannot be determined in advance by counting the number of blob peaks and using a model that has one species peak for each blob peak.

As noted above, the preferred choice for the candidate peak in a blob is the dominant peak in the blob. However, in some cases, the dominant peak may be a peak within the blob with adjacent peaks on both sides that prevent the determination of the parameters of a single peak model. When the dominant peak has other peaks on each side of the dominant peak, obtaining a good estimate of the $\sigma$ and the position of the peak center and the amplitude can present significant challenges for a one-peak model.

Figure 6:
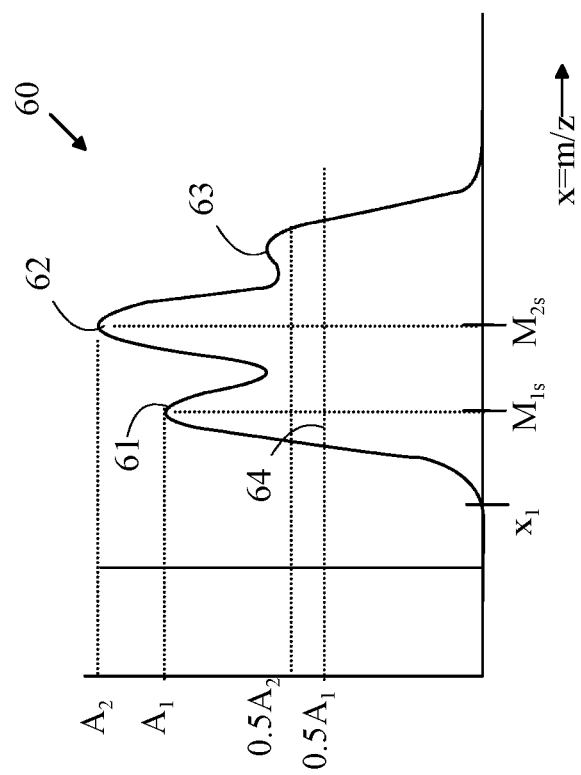
FIG. 6 illustrates a blob having three peaks in which the maximum associated with the dominant blob peak is between two other maxima that are associated with two underlying peaks.

Refer now to FIG. 6, which illustrates a blob having three peaks in which the maximum associated with the dominant blob peak 62 is between two other maxima shown at 61 and 63 that are associated with two underlying peaks. As can be seen from the drawing, traversing blob peak 62 in either direction looking for the half-height points encounters another peak before the half-height points are reached. Hence, the blob values in the region of blob peak 62 are unlikely to yield a good fit in the one-peak model, as the tails from surrounding peaks distort the underlying species peak. Hence, the data processing system will go on to examine the side blob peaks shown at 61 and 63.

Consider the case when blob peak 61 is examined. The half-height point on the left side of blob peak 61 is reached without traversing any other peaks. Hence, this peak could be a candidate for a single peak model. To determine if a good fit can be obtained, the data processing system assumes that $A_1$ is the height of the single model peak and $M_{1s}$ is the center of the peak. Once again, a number of different $\sigma$ values are computed from the amplitude of blob peak 61 for different m/z values on the left edge. If the $\sigma$ value is constant over a range of m/z values on this edge, a good fit is likely, and the species peak can be removed from the blob as discussed above.

Consider a peak at the edge of the blob that is to be removed. This peak will be referred to as the "edge peak". The edge peak is being distorted by a neighboring peak which has a tail that extends far into the edge peak. If an approximation to the tail of the neighboring peak that extends into the edge peak can be obtained, the $\sigma$ of the edge peak can be determined and used to generate the model of the edge peak that can then be subtracted from the blob.

Consider the case in which none of the blob peaks allows a one-peak model to be generated. If the dominant peak or edge peaks cannot be satisfactorily fitted to a single peak model, a multiple peak model can be utilized.

When no peak in the blob can be fit to a single species model, a higher order model in which a portion of the blob is fitted to a two or three species peak model must be utilized. The goal of the higher model is still to find the parameters of a single species peak that can be subtracted from the blob. The additional peaks in the model provide approximations to the tails of species peaks that are distorting the species peak of interest and correct for the interfering tails of the adjacent species peaks. If the blob peak of interest has a single adjacent species peak that is causing the distortion, a two-species peak model is utilized. If the peak of interest has two adjacent peaks, the three-species peak model is utilized.

Refer again to FIG. 6. Consider the case in which blob peak 61 is to be removed utilizing a two species peak model of the form:

$$a(x) = A_1 e^{-(M_1-x)^2/2\sigma_1^2} + A_2 e^{-(M_2-x)^2/2\sigma_2^2} \quad (2)$$

Here, a(x) is the abundance as a function of m/z. To simplify the notation, m/z has been replaced by the variable x. In this notation, $M_1$ and $M_2$ are the centers of the two peaks in units of m/z, respectively. If the blob were a two-peak blob, this model would provide the parameters for both underlying species peaks accurately. However, if there are additional species peaks beyond the peak that is adjacent to the edge species peak in question, the model will fail to accurately represent the second species peak, as that model will not take into account the species peaks beyond the second peak; however, it may provide sufficient correction for the distortions introduced into the edge blob peak by the interfering peak to allow the parameters of the edge species peak to be accurately determined.

Referring to FIG. 6, it will be assumed that the model shown in Eq. (2) is to be used to compute the parameters of the species peak associated with blob peak 61 in blob 60. That is, the species peak associated with blob peak 61 is the first peak, and the species peak associated with blob peak 62 is the second peak. To remove the edge peak, the model must be fit to the blob data associated with the edge peak and a significant portion of the blob data associated with the interfering peak(s). The portion of the blob that is used to fit the model needs to be substantially free of values for species peaks corresponding to blob peak 63. The portion of the blob between the blob peaks 61 and 62 and the leading edge of blob peak 61 provide blob abundance values that only depend on the species peaks under blob peaks 61 and 62.

The end of the edge peak can be estimated from the position of the maximums, $M_{1s}$ and $M_{2s}$, and the half-width at half maximum shown at 64. The half-width at half-maximum can be used to compute an approximation to $\sigma_1$. The upper limit of the data to be fit is then taken as $M_{1s}+3\sigma_1$. Hence, the fit is performed from $x_1$ to the larger of $M_{2s}$ or $M_{1s}+3\sigma_1$.

Since the model is non-linear in the parameters of interest, the fit must be performed as a search within the expected ranges of the parameters. Accordingly, it is advantageous to minimize the number of parameters and to provide good approximations for the starting values of these parameters in the search. The positions of the blob peaks 61 and 62 shown at $M_{1s}$ and $M_{2s}$, are used as the starting values for the species peak centers, $M_1$ and $M_2$ in the model. The amplitudes of these maximums are used as the starting values for $A_1$ and $A_2$ in the model. The widths of the species peaks are expected to be substantially equal within the blob, since the species peak widths are determined by resolution of the mass spectrometer which should be approximately constant as a function of m/z in the region of the blob. Hence, $\sigma_2$ is set to $\sigma_1$, and the starting value is set to the approximation to $\sigma_1$ determined from the half-width at half maximum.

Search algorithms for optimizing the values of the model parameters are well known in the art, and hence, will not be discussed in detail here. Once the optimum values for the parameters are determined, the single peak portion of the model corresponding to the blob peak of interest can be examined to test the validity of the model fit. For example, the least squares residual for the blob data points in the region of the blob peak of interest can be examined to verify the accuracy of the fitted model for the underlying single species peak. If fit for this peak is validated, the model peak is subtracted from the blob. The remainder of the blob can then be analyzed to remove the next peak starting with the search for a single peak model, and so on.

If the target peak is surrounded by adjacent peaks, then a three-species peak model is preferred if a single peak model fails. The fitting procedure is analogous to that discussed above with respect to the two-species peak model. After the three-species peak model parameters are determined, the second peak in the model is subtracted from the blob leaving two residual blobs.

Since the species peaks are removed by an iterative process, ensuring that the model species peak being removed is a good representation of the underlying species peak is important. In the above-described embodiments, the amplitude of the model peak is set to the height of the corresponding blob peak. In the case of a single peak model, this can lead to an overestimate of the amplitude of the underlying Gaussian, since blob peak height is the sum of the model amplitude and the tail of the neighboring peak under the blob peak. This does not pose a significant problem for a multi-peak model, since the model parameters, including the peak amplitudes are determined by the search procedure. However, in the above described methods, the amplitude of the model species peak is set to the height of the blob peak. A discrepancy between the actual model peak amplitude and the amplitude of the blob peak can result in the single species peak model failing the consistency tests. In one embodiment of the present invention, the consistency tests are repeated for a number of different values for the model species peak amplitude. The maximum of the model species peak amplitudes to be tested is the blob peak height.

The validity of the single peak models determined from the blob values can also be tested by examining the residual blob after the model species peak has been subtracted. The region of the residual blob in the area of the species peak should be non-negative; hence, if the area is less than the minimum abundance value, the amplitude of the model species peak was too large. A search for the correct species peak amplitude starts with the amplitude obtained from the corresponding blob peak, and decreases at each successive test. When the area of the residual blob at the species peak location is reduced to the minimum abundance value, the search can stop and utilize the resultant species amplitude.

The above-described embodiments start by selecting a blob peak. The abundance values of a blob are typically a sequence of digital values of the form b(i), for i=$b_{min}$ to $b_{max}$. In one exemplary embodiment, the present invention utilizes two different peak algorithms in identifying a blob peak. A blob peak is defined to be a three-point blob peak at m/z index, i, if $ba(i-1)<ba(i)>ba(i+1)$ and $ba(i) \geq$ peak threshold.

A blob peak is defined to be a five-point peak at index i if $ba(i-2)<ba(i-1)<ba(i)>ba(i+1)>ba(i+2)$ and $ba(i) \geq$ peak threshold.

In general, the peak threshold is greater than the blob threshold discussed above.

The set of three-point blob peaks contains all of the blob peaks in a blob except peaks for which the peak value consists of two points of equal abundance; however, some of these may be the result of noise. Five-point peaks are less likely to be the result of noise; however, peaks may be missed. It should be noted that each five-point peak is also a three-point peak. In the absence of noise, scanning the blob for three-point peaks identifies all of the blob peaks. However, in the presence of noise, some degree of preprocessing is useful in preventing noise peaks from being chosen as blob peaks. It should be noted that the spectrum from the mass spectrometer is subject to instrument noise from the detector and from noise from the counting statistics.

Figure 7:
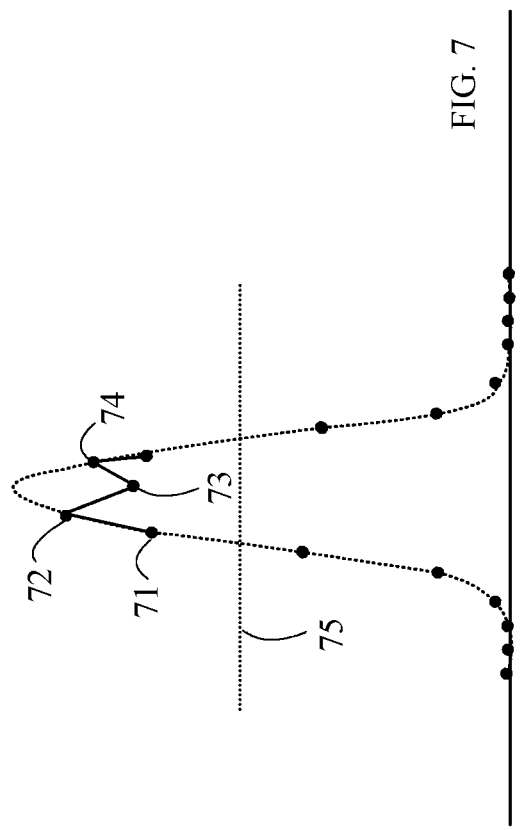
FIG. 7 illustrates a peak that is mistakenly viewed as two peaks if a three-point peak identification algorithm is used.

In one aspect of the invention, the blob data is preprocessed to remove peaks that are the result of noise. Refer now to FIG. 7, which illustrates a peak that is mistakenly viewed as two peaks if a three-point peak identification algorithm is used. First, it should be noted that the data from the mass spectrometer is sampled, and hence, the measured data is a sequence of discrete points such as points 71-74. The dashed curve represents a Gaussian peak model that fits all of the points with the exception of point 73. Point 73 is the result of the finite statistics of the individual points and/or noise in the surrounding points. A three-point peak finding algorithm identifies two closely spaced peaks at 72 and 74 that share a common point 73. A pair of three-point peaks that share a common point and are above a predetermined minimum peak threshold 75 will be referred to as a two-eared peak in the following discussion. In one aspect of the invention, the blob is first searched for two-eared peaks. When a two-eared peak is found, the peak is corrected by replacing the common point with the value obtained by a least square fit of a parabola through the remaining four points. The resulting corrected peak is a five-point peak, with its blob peak at the m/z value between 72 and 74.

In another aspect of the invention, the blob data is first filtered through a low pass filter to suppress noise prior to searching for peaks in the blob. The bandpass of the filter must be high enough to prevent the filter from substantially altering the estimates of the underlying peaks in the spectrum and low enough to suppress the noise. For example, the filter can fit each point in the spectrum and the four surrounding points to a parabola and replace the point by the value of the parabola at that m/z location.

In another aspect of the invention, the blobs are low pass filtered and the peak removal algorithm is applied to the smoothed data. As noted above, errors in the amplitude of the blob peaks can lead to failed fits for the species peaks, because noise near the blob peak can cause errors in the assumed amplitude of the species peaks. By pre-smoothing all of the blob, this type of error is significantly reduced.

In the above-described embodiments, the species peaks were modeled as Gaussian distributions; however, other distributions can also be utilized. For example, two-slope Gaussian, Gamma, Poisson and, Rayleigh distributions may more accurately represent the ideal species peak shapes. However, the differences are relatively small, and the Gaussian distribution has the advantage of being defined over the entire m/z axis, while having negligible values become negligible outside of the ±3σ width. Finally, the parameters of the Gaussian distribution are easy to compute from the peak position and value and the value of one additional point off of the peak.

The present invention also includes a computer readable medium that stores instructions that cause a data processing system to execute the method of the present invention. A computer readable medium is defined to be any medium that constitutes patentable subject matter under 35 U.S.C. 101 and excludes any medium that does not constitute patentable subject matter under 35 U.S.C. 101. Examples of patentable media include non-transitory media such as computer memory devices that store information in a format that is readable by a computer or data processing system.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A method for operating a data processing system to find species peaks in a mass spectrum comprising an ordered set of measurements characterized by an abundance of species as a function of a mass/charge ratio (m/z), said method comprising:
   (a) processing a sample in a mass spectrometer to produce said mass spectrum;
   (b) selecting a candidate blob from said mass spectrum, said candidate blob being characterized by a plurality of species peaks that overlap to produce said candidate blob;
   (c) searching the candidate blob to find a plurality of blob peaks;
   (d) selecting a candidate blob peak from said plurality of blob peaks for characterization;
   (e) searching the candidate blob peak to find a side blob peak of the plurality of blob peaks that overlaps with the candidate blob peak;
   (f) approximating a first species peak corresponding to said candidate blob peak and a second species peak corresponding to said side blob peak, by generating a multi-species peak model and fitting the multi-species peak model to a portion of said candidate blob peak and a portion of said side blob peak; and
   (g) subtracting said first species peak and said second species peak from said candidate blob.

2. The method of claim 1 wherein said plurality of blob peaks are characterized by a dominant blob peak and wherein said dominant blob peak is selected as said candidate blob peak.

3. The method of claim 1 wherein said plurality of blob peaks are characterized by first and second edge blob peaks, said candidate blob peak being one of said first and second edge blob peaks.

4. The method of claim 1, comprising:
   after the subtracting of said first species peak and said second species peak, selecting an additional candidate blob peak from said plurality of blob peaks for characterization;
   searching the additional candidate blob peak to find an additional side blob peak of the plurality of blob peaks that overlaps with the additional candidate blob peak;
   if an additional side blob peak is not found, (i) approximating a third species peak corresponding to said additional candidate blob peak by generating a single-species peak model and fitting the single-species peak model to a portion of said additional candidate blob peak, and (ii) subtracting said third species peak from said candidate blob;

if an additional side blob peak is found, (i) approximating a third species peak corresponding to said additional candidate blob peak and a fourth species peak corresponding to said additional side blob peak, by generating a multi-species peak model and fitting the multi-species peak model to a portion of said additional candidate blob peak and a portion of said additional side blob peak, and (ii) subtracting said third species peak and said fourth species peak from said candidate blob.

5. The method of claim 1 wherein said candidate blob peak is displayed with said species peaks associated with said candidate blob peak superimposed on said candidate blob peak.

6. The method of claim 1 wherein said multi-species peak model is characterized by a plurality of model parameters, said candidate blob peak is characterized by a blob peak amplitude and a center m/z value, and approximating said first species peak comprises determining said plurality of model parameters from said blob peak amplitude, said center m/z value, and an amplitude of said candidate blob peak at a point different from said center m/z value.

7. The method of claim 1 wherein said multi-species peak model comprises a function selected from the group consisting of: Gaussian, two-slope Gaussian, Gamma, Poisson and Rayleigh functions.

8. The method of claim 1 wherein said multi-species peak model comprises a two-species peak model.

9. The method of claim 1 wherein:
said side blob peak is a first side blob peak;
searching the candidate blob comprises finding a second side blob peak on an opposite side of said candidate blob peak to said first side blob peak;
the approximating comprises approximating a third species peak corresponding to said second side blob peak, by fitting the multi-species peak model additionally to a portion of said second side blob peak; and
the subtracting comprises subtracting said third species peak from said candidate blob.

10. The method of claim 1 wherein said candidate blob is filtered through a low-pass filter prior to selecting said candidate blob peak for characterization.

11. The method of claim 1 wherein said data processing system is part of a built-in controller that controls the mass spectrometer.

12. A computer readable medium comprising instructions that cause a data processing system to execute the method of claim 1.

13. The computer readable medium of claim 12 wherein said plurality of blob peaks are characterized by a first edge blob peak and a second edge blob peak, said candidate blob peak being one of said first and second edge blob peaks.

14. The computer readable medium of claim 12 wherein steps (d)-(g) are repeated until there are no more peaks in said candidate blob that can be approximated by a species peak model.

15. The computer readable medium of claim 12 wherein said multi-species peak model is characterized by a plurality of model parameters, said candidate blob peak is characterized by a blob peak amplitude and a center m/z value, and approximating said first species peak comprises determining said plurality of model parameters from said blob peak amplitude, said center m/z value, and an amplitude of said candidate blob peak at a point different from said center m/z value.

16. The computer readable medium of claim 12 wherein said multi-species peak model comprises a selected from the group consisting of: Gaussian, two-slope Gaussian, Gamma, Poisson and Rayleigh functions.

17. The computer readable medium of claim 12 wherein said multi-species peak model comprises a two-species peak model.

18. The computer readable medium of claim 12 wherein:
said side blob peak is a first side blob peak;
searching the candidate blob comprises finding a second side blob peak on an opposite side of said candidate blob peak to said first side blob peak;
the approximating comprises approximating a third species peak corresponding to said second side blob peak, by fitting the multi-species peak model additionally to a portion of said second side blob peak; and
the subtracting comprises subtracting said third species peak from said candidate blob.

19. The computer readable medium of claim 12 wherein said candidate blob is filtered through a low-pass filter prior to selecting said candidate blob peak for characterization and removal.

20. A mass spectrometer comprising the computer readable medium of claim 12.

* * * * *